(12) United States Patent
Eidenschink

(10) Patent No.: US 10,631,863 B2
(45) Date of Patent: Apr. 28, 2020

(54) APPARATUS FOR HEART VALVE REPAIR

(71) Applicant: St. Jude Medical, Cardiology Division, Inc., St. Paul, MN (US)

(72) Inventor: Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1206 days.

(21) Appl. No.: 14/376,344

(22) PCT Filed: Feb. 1, 2013

(86) PCT No.: PCT/US2013/024296
§ 371 (c)(1),
(2) Date: Aug. 1, 2014

(87) PCT Pub. No.: WO2013/116610
PCT Pub. Date: Aug. 8, 2013

(65) Prior Publication Data
US 2015/0045815 A1    Feb. 12, 2015

Related U.S. Application Data

(60) Provisional application No. 61/593,437, filed on Feb. 1, 2012.

(51) Int. Cl.
*A61B 17/10* (2006.01)
*A61B 17/064* (2006.01)
(Continued)

(52) U.S. Cl.
CPC ........ *A61B 17/10* (2013.01); *A61B 17/00234* (2013.01); *A61B 17/0644* (2013.01);
(Continued)

(58) Field of Classification Search
CPC ................ A61B 17/10; A61B 17/0644; A61B 2017/081; A61B 2017/00349;
(Continued)

(56) References Cited

U.S. PATENT DOCUMENTS 4,857,046 A * 8/1989 Stevens ..................... A61B 1/12
604/22
4,964,864 A * 10/1990 Summers .............. F04C 13/001
600/16

(Continued)

FOREIGN PATENT DOCUMENTS

| WO | 00/03759 A2 | 1/2000 |
|---|---|---|
| WO | 2006120464 A2 | 11/2006 |
| WO | 2007112033 A2 | 10/2007 |

OTHER PUBLICATIONS

Arndt, A. et al., "Suction-Free Operation of an Axial Flow Blood Pump With a Magnetically Uspended Rotor", ASAIO Journal, vol. 49, No. 2, Mar. 1, 2003, p. 156, XP055416807.
(Continued)

*Primary Examiner* — Tan-Uyen T Ho
*Assistant Examiner* — Chima U Igboko
(74) *Attorney, Agent, or Firm* — Lerner, David, Littenberg, Krumholz & Mentlik, LLP

(57) ABSTRACT

A device (10) for repair of a heart valve leaflet includes an elongated body (12) having a lumen (16) extending therethrough in a longitudinal direction, a proximal end, an open distal end (19). A core (11) is disposed within the lumen, and is operable to spin about an axis extending in the longitudinal direction. The spinning of the core draws a portion of the heart valve leaflet into the lumen through the open distal end of the body and secures the portion of the heart valve leaflet to the core in a gathered configuration.

13 Claims, 5 Drawing Sheets

(51) Int. Cl.
*A61B 17/00* (2006.01)
*A61B 17/12* (2006.01)
*A61F 2/24* (2006.01)
*A61B 17/08* (2006.01)
*A61B 90/00* (2016.01)

(52) U.S. Cl.
CPC ........ *A61B 17/08* (2013.01); *A61B 17/12013* (2013.01); *A61F 2/2454* (2013.01); *A61B 90/06* (2016.02); *A61B 2017/00243* (2013.01); *A61B 2017/00292* (2013.01); *A61B 2017/00349* (2013.01); *A61B 2017/00685* (2013.01); *A61B 2017/00783* (2013.01); *A61B 2017/00867* (2013.01); *A61B 2017/0649* (2013.01); *A61B 2017/081* (2013.01); *A61B 2017/12018* (2013.01)

(58) Field of Classification Search
CPC .......... A61B 2017/00685; A61B 17/02; A61B 2017/348; A61F 2/2454; A61M 1/10; A61M 1/0082; A61M 27/00
See application file for complete search history.

(56) References Cited

U.S. PATENT DOCUMENTS

| | | | | |
|---|---|---|---|---|
| 5,407,427 A | * | 4/1995 | Zhu | A61B 17/0281 604/26 |
| 5,507,795 A | * | 4/1996 | Chiang | A61B 17/320783 606/167 |
| 5,891,094 A | * | 4/1999 | Masterson | A61B 18/08 604/113 |
| 5,899,915 A | * | 5/1999 | Saadat | A61B 17/32002 604/22 |
| 2003/0009157 A1 | * | 1/2003 | Levine | A61B 18/26 606/7 |
| 2004/0138682 A1 | | 7/2004 | Onuki et al. | |
| 2004/0219028 A1 | * | 11/2004 | Demarais | A61B 17/320725 417/53 |
| 2005/0159677 A1 | * | 7/2005 | Shabaz | A61B 10/0275 600/567 |
| 2005/0251160 A1 | * | 11/2005 | Saadat | A61B 17/0401 606/153 |
| 2007/0225734 A1 | | 9/2007 | Bell et al. | |
| 2008/0287983 A1 | * | 11/2008 | Smith | A61B 17/00234 606/192 |
| 2009/0105728 A1 | * | 4/2009 | Noda | A61B 17/12013 606/139 |
| 2011/0301634 A1 | | 12/2011 | Aklog et al. | |
| 2012/0109159 A1 | * | 5/2012 | Jordan | A61B 17/1227 606/142 |

OTHER PUBLICATIONS

International Search Report and Written Opinion for Application No. PCT/US2013/024296 dated Jul. 23, 2013.

* cited by examiner

APPARATUS FOR HEART VALVE REPAIR

CROSS-REFERENCES TO RELATED APPLICATIONS

The present application is a national phase entry under 35 U.S.C. § 371 of International Application No. PCT/US2013/024296, filed on Feb. 1, 2013, published in English, which claims priority from U.S. Patent Application No. 61/593,437, filed Feb. 1, 2012, all of which are hereby incorporated herein by reference.

BACKGROUND OF THE INVENTION

The present invention is related to tissue repair, and more particularly to devices, systems, and methods for repair of a heart valve leaflet.

Properly functioning heart valves can maintain unidirectional blood flow in the circulatory system by opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be ruptured. As a result, the valve does not close normally and the unsupported valve leaflet may bulge back, or "prolapse," into the left atrium like a parachute. Thus, as the ventricle contracts, the abnormal leaflet may be propelled backwards, beyond its normal closure line and into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There, therefore, is a need for further improvements to the current techniques for treating heart valve leaflet prolapse. Among other advantages, the present invention may address one or more of these needs.

BRIEF SUMMARY OF THE INVENTION

One aspect of the disclosure provides a device for repair of a heart valve leaflet including an elongated body including a proximal end, a distal end and a lumen having an open end at the distal end of the body. The device further includes a core disposed within the lumen, the core having a longitudinal axis and being operable to spin within the lumen about the longitudinal axis. The spinning of the core draws a portion of the heart valve leaflet into the lumen through the open end and secures the portion of the heart valve leaflet to the core in a gathered configuration.

In one example, the core includes a rib, at least a portion of the rib including a resilient material. The resilient material may form a helical pattern on the rib. In this example, the resilient material may include rubber. In another example, the device further includes a torque sensor connected to the core and operable to terminate spinning of the core upon sensing a predetermined maximum torque. The spinning of the core may draw blood into the lumen through the open end, and the elongated body includes a plurality of apertures for expelling the blood from the lumen. In another example, the core includes a proximal end, a distal end and a sidewall between the proximal end and the distal end, the sidewall having a circumference which decreases in size from the proximal end to the distal end. In another example, the device includes a wire operable to pull a portion of the heart valve leaflet toward the open end of the lumen. In another example, the core includes a proximal end, a distal end and a bore extending from the proximal end to the distal end, the wire being disposed through the bore.

Another aspect of the disclosure provides a method of repairing a heart valve leaflet. The method includes positioning a repair device adjacent the heart valve leaflet. The repair device includes an elongated body having a proximal end, a distal end and a lumen having an open end at the distal end of the body, and a core disposed within the lumen, the core having a longitudinal axis. The core is spun within the elongated body about the longitudinal axis in a first direction to draw a portion of the heart valve leaflet into the lumen through the open end. The portion of the heart valve leaflet is secured to the core in a gathered configuration. At least one clip is applied to the portion of the heart valve leaflet in the gathered configuration and the heart valve leaflet is released from the elongated body In one example, the method includes sensing the torque exerted by the spinning core and terminating the spinning step upon sensing a predetermined maximum torque. In another example, the spinning step includes capturing the portion of the heart valve leaflet by a resilient material on a rib of the core. In another example, the spinning step draws blood into the lumen through the open end, and the method further includes expelling the blood from the lumen through a plurality of apertures in the elongated body. In another example, the method includes extending a wire through the core, a distal portion of the wire having a hook-shape configuration. The distal portion of the wire may be drawn toward the core to pull a portion of the heart valve leaflet toward the open end of the lumen. In another example, the method includes retracting the elongated body after capturing the heart valve leaflet to expose additional tissue for coupling the at least one clip at the location of the exposed additional tissue. In another example, a wire is extended through the core, a distal portion of the wire having a hook-shape configuration and the distal portion of the wire is drawn toward the core to pull a portion of the heart valve leaflet toward the open end of the lumen. In another example, the releasing step includes spinning the core in a second direction opposite the first direction to release the portion of the heart valve leaflet from the core.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may also be useful in the repair of other types of cardiac valves or in the gathering and securing of other types of loose body tissue.

Figure 1:
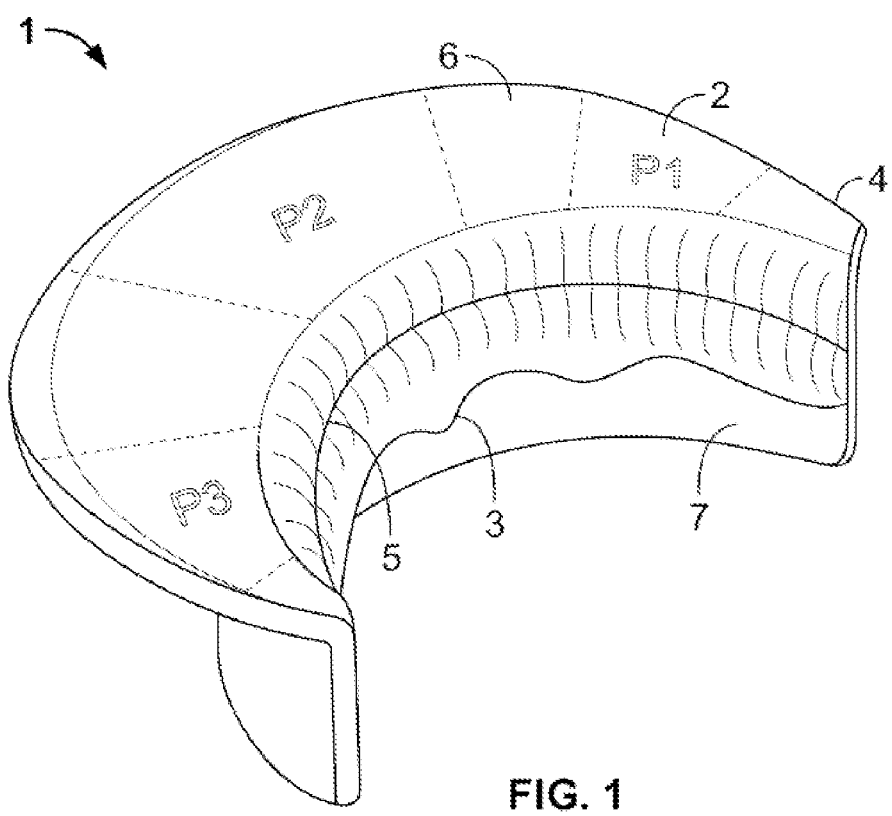
FIG. 1 is a diagrammatic perspective view of the posterior leaflet of a mitral valve.

As shown in FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2A:
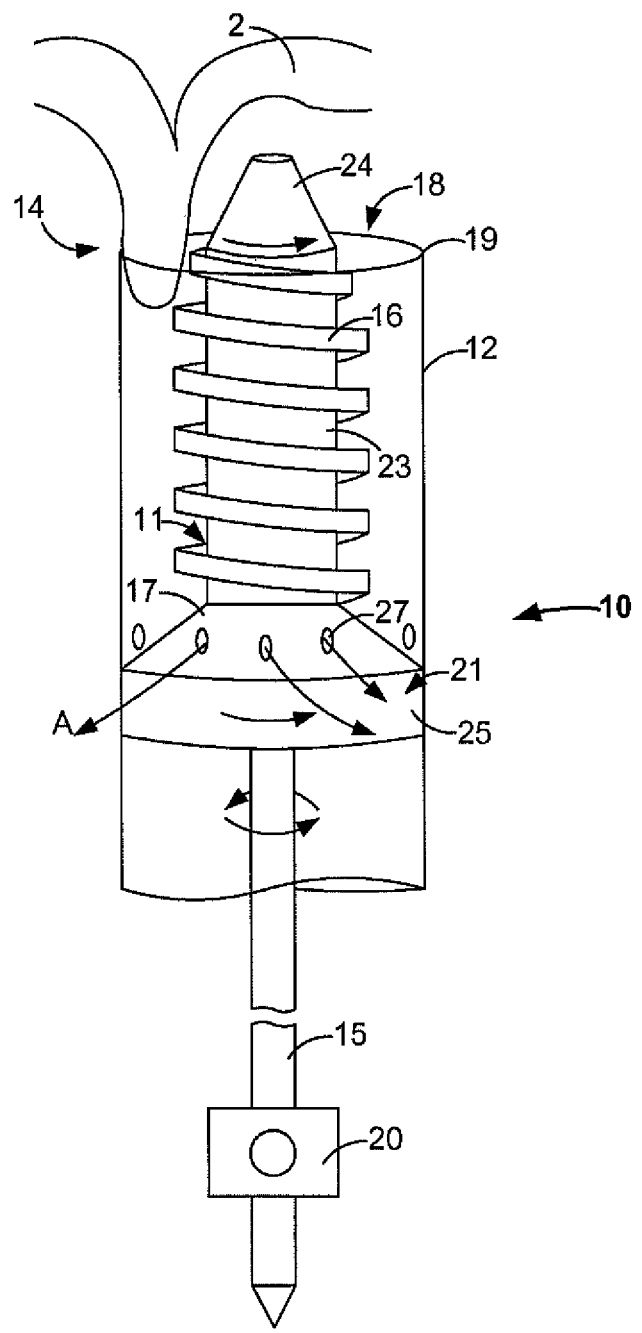
FIG. 2A is a highly schematic front view of a device for repairing mitral valve leaflets in accordance with one embodiment of the present invention.

Referring to FIG. 2A, an exemplary device 10 for repair of heart valve leaflet tissue may include an elongated catheter 12 adapted to be inserted through the left atrium of a human heart so that a distal portion 14 of the catheter may reach the patient's mitral valve for repair thereof. Though FIG. 2A illustrates the device 10 being employed near the posterior leaflet 2, it may likewise be used to repair the anterior leaflet 3 or any other suitable tissue within the heart or elsewhere in the body.

The catheter 12 may be formed of any hollow tube, shaft or sheath defining a longitudinal lumen 18 with an open distal end 19. It will be understood that the shape and size of the open distal end 19 may be modified as necessary.

A core 11 is disposed for rotation within the lumen 18 in the distal portion 14 of catheter 12. The core 11 may be coupled through a driveshaft 15 to a motor (not shown) for spinning the core at a desired speed. The driveshaft 15 may extend to a handle (not shown) at the proximal end of catheter 12. By depressing, sliding or rotating an actuating member, such as a button or slide on the handle, the motor may be turned on to rotate the driveshaft 15, and with it, the core 11. The motor may be adapted to spin the core 11 at a speed sufficient to create an eddy or vortex near the open distal end 19 of catheter 12. The eddy or vortex created preferably is sufficiently strong to cause a suction force or pulling force to act on loose chordae or loose leaflet portions 2 or 3. In order to generate a sufficient suction force, core 11 preferably spins at a frequency greater than about 1,000 rpm, and more preferably at a frequency between about 1,000 rpm and about 100,000 rpm.

Figure 2B:
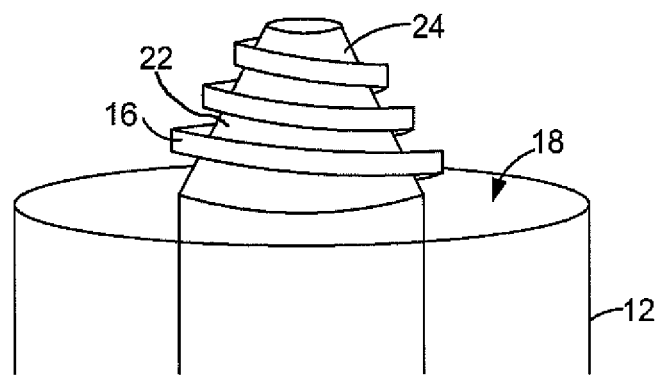
FIG. 2B is a highly schematic front view of the distal end of a device for repairing mitral valve leaflets in accordance with one variation of the embodiment of FIG. 2A.

Core 11 may have a variety of different shapes or profiles. For example, core 11 may have a generally cylindrical body 23 with a frustoconical distal tip 24. As seen in FIG. 2B, the distal tip 24 includes sidewalls 22 that decrease in circumference from the cylindrical body 23 to the distal end of the core 11. In a variant hereof, the entire core 11 may be slightly tapered from the proximal end of the core to its distal end. Tapering at least the distal tip of the core 11 provides an improved profile of the pulling force acting on the loose tissue. The extent of the tapering of the core 11 may be chosen based on the amount of pulling force desired.

Core 11 may further include a body 21 defining an outwardly tapered surface 17 spaced proximally from distal tip 24. Surface 17 may taper outwardly to a substantially cylindrical wall 25 that provides a very small clearance from the inner surface of catheter 12. Surface 17 diverts any fluids that may be drawn into lumen 18 radially outward toward the inner surface of catheter 12, but the small clearance between the wall 25 and the catheter inner surface minimizes the amount of fluid that may pass proximally of body 21. When part of core 11, either by being formed integrally therewith or by being formed separately and connected thereto, body 21 will rotate along with the rest of the core, with the clearance between the wall 25 and the inner surface of catheter 12 being sufficient to allow for free rotation without drag or binding. It will be appreciated, however, that body 21 may be formed as a separate element and fixed in a stationary position within lumen 18.

Turning back to FIG. 2A, the core 11 may further include one or more ribs 16 arranged about at least the cylindrical body 23 of the core for grabbing loose tissue, such as that of leaflets 2 or 3, that is drawn into the lumen 18. The ribs 16 may be attached to the core 11 or formed as an integral part of the core, and may be formed of a soft rubber, silicone, urethane or other suitable material. The ribs 16 may have a rough surface or protruding members to enhance their ability to grab loose tissue. It will be understood that the shape and size of the ribs 16 may be varied as desired. For example, ribs 16 may be formed in the shape of a continuous helical corkscrew, or in the form of a plurality of rings spaced axially apart from one another along the length of the core 11. Still further, the ribs 16 may be formed by discontinuous bumps or ridges positioned about the core 11. Thus, various configurations of the ribs 16 may be used and the scope of the disclosure is not limited to circular or helical structures.

In order to expel any fluids that may be drawn into lumen 18 along with loose tissue, catheter 12 may include a plurality of apertures 27. Thus, apertures 27 serve to expel blood from the lumen 18 to the exterior of the catheter, as depicted by arrows "A" in FIG. 2A. The plurality of apertures may be spaced substantially uniformly around the circumference of catheter 12 at about the same distance from open end 19. It will be understood, however, that multiple configurations or arrangements of the apertures 27 may be disposed on the catheter 12. For example, the apertures 27 may be evenly arranged near the distal end of the catheter 12. Alternatively, the apertures 27 may be arranged at multiple longitudinal positions forming several rings on the catheter 12. In a preferred arrangement, apertures 27 may be disposed adjacent the outwardly tapered surface 17 of body 21. In this manner, the tapered surface 17 may direct blood and other fluids radially outward toward the wall of catheter 12, where they may exit the catheter through apertures 27. The number and configuration of apertures 27 may be chosen depending on the frequency at which the core 11 spins and the expected volume of blood and other fluids being drawn into the lumen 18.

An optional torque sensor 20 may also be included and coupled to the driveshaft 15. The torque sensor 20 may monitor the torque exerted on the core 11 and function as a safety mechanism for the device 10. Once a predetermined maximum torque has been reached, the torque sensor 20 may send a signal to shut off power to the drive motor. Alternatively, torque sensor 20 may include a clutch mechanism or may send a signal to a separate clutch mechanism to disengage the driveshaft 15 from the drive motor, or torque sensor 20 may act in some other manner to stop the driveshaft 15 from rotating. The predetermined maximum torque may be defined by a user input and changed based on the extent of the loose tissue and/or on data relating to the patient (e.g., anthropometric data).

All or part of the distal portion of device 10, such as core 11, the distal portion 14 of distal catheter 12, and/or ribs 16, may be made of one or more echogenic materials to enable these structures to be more easily visualized using three-dimensional echocardiography while the device is in use in a patient. This allows the physician or surgeon to more easily manuever, monitor and retract the device 10 without any injury to the patient.

To use the device 10 for transcatheter repair of heart valve leaflet tissue, the catheter 12 may be inserted into the patient and advanced to the mitral valve, preferably using a trans-septal approach. That is, the catheter 12 may be advanced from the femoral vein through the iliac vein, the inferior vena cava, and the right atrium, and across the septum wall into the left atrium, until the distal portion 14 thereof extends between the posterior leaflet 2 and the anterior leaflet 3 of the mitral valve 1. This route requires the least amount of bending or turning and provides the most direct route to the mitral valve leaflets. Minimizing the number of turns may facilitate control of the distal portion 14 of the catheter 12. If the distal portion 14 includes echogenic materials, the distal portion may be guided to a position against a leaflet at the coaption line 5 using the assistance of three-dimensional echocaradiography to visualize the distal portion 14 and other components of the device 10.

Once device 10 has reached the leaflets 2 and 3, the core 11 may be rotated by actuating the motor through operation of the actuating member on the device handle. With the device spinning at the appropriate frequency, a vortex is created near the open distal end 19 of catheter 12 that pulls the loose leaflet 2 or 3, or chordae tendineae toward and into the lumen 18.

It will be appreciated that, as the core 11 spins, the vortex created draws into lumen 18 not only loose chordae and loose leaflet portions 2 or 3, but also blood and other fluids. Any such fluid drawn into lumen 18 may be expelled to the exterior of catheter 12 through apertures 27. Thus, the device 10 can be used without disturbing the in vivo environment and without leading to a loss of blood or other fluids.

Once the desired leaflet 2 or 3 has been drawn into the lumen 18, the loose tissue of the leaflet will become wrapped around or otherwise gripped by the ribs 16. When enough loose tissue has been wrapped around the ribs 16, the torque sensor 20 may detect a predetermined maximum torque and stop rotation of the core 11 as described above. A mass of gathered tissue 42 may thus be formed within the lumen 18, resulting in a tightening in the remaining portions of the leaflet.

Figure 4:
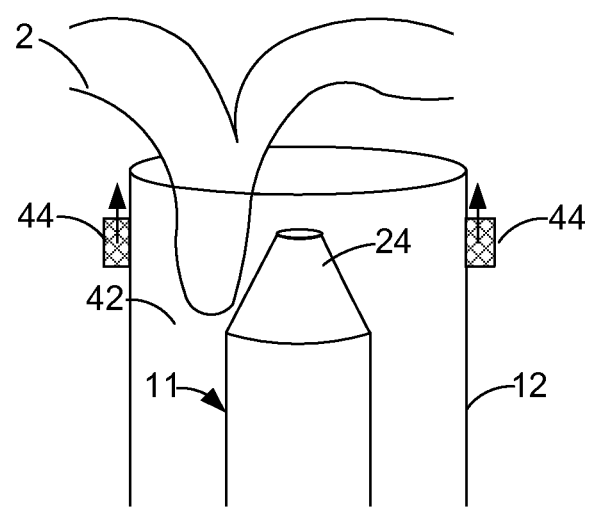
FIGS. 4 and 5 are diagrammatic views showing the steps of gathering heart valve leaflet tissue and applying a clip to same using the device of FIG. 2A.
Figure 5:
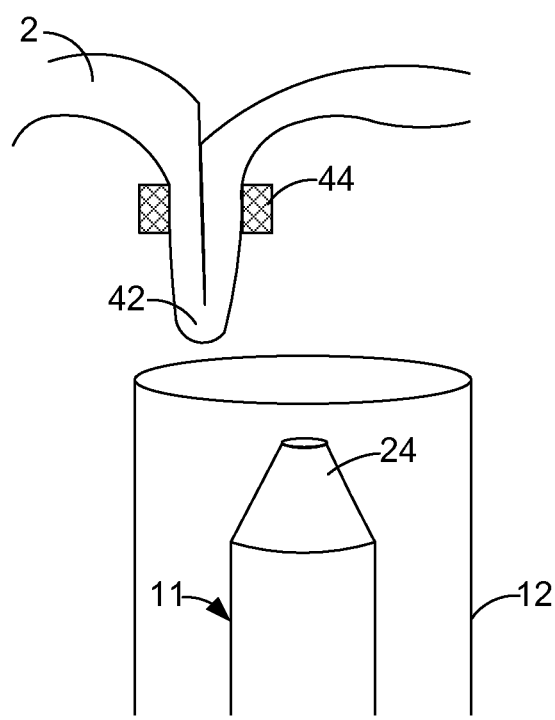
Figure 6:
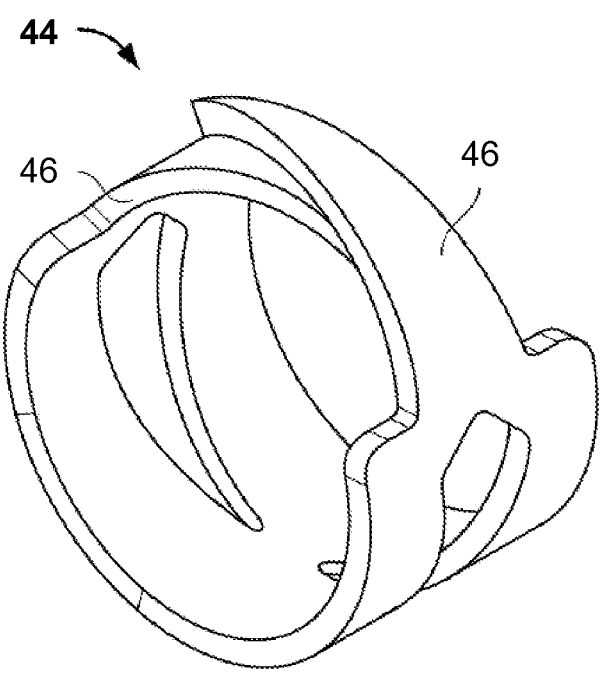
FIG. 6 is a plan view of one example of a clip of, shown in the closed position.

Turning to FIGS. 4-6, once a sufficient amount of loose tissue has been gathered, the gathered tissue 42 may be secured. Securing of the gathered tissue 42 may be accomplished through the use of one or more fasteners, such as, for example, a clip 44 as shown in detail in FIG. 6. Each clip 44 may be in the form of a discontinuous ring having overlapping ends 46. Clip 44 may be formed from a shape-memory material, such as nitinol, such that when placed in an expanded condition with the ring ends 46 no overlapping (or overlapping by a lesser extent), the ring will be biased to curl into a collapsed or rest condition. One or more clips 44 may be disposed in an expanded condition about catheter 12 adjacent the distal end 19 thereof. After loose tissue has been gathered a secondary tube (not shown), slidably assembled around catheter 12, may be used to push clips 44 one at a time off of catheter 12, clip 44 may be slid off and onto the gathered tissue 42. No longer being constrained by the catheter 12, the clips 44 may return to their collapsed condition, tightly engaging the gathered tissue 42 and securing it in a gathered configuration. It will be appreciated that, instead of clip 44, a suture, clasp, staple or other suitable fastener may be used to hold the gathered tissue 42 in the gathered configuration.

The operation of device 10 as described above may not gather a sufficient amount of tissue to secure with a clip 44 or other fastener or to apply multiple fasteners to. In such event, the device 10 may be pulled slightly in the proximal direction. Because the tissue is fastened to the ribs 16, pulling the device 10 proximally exposes additional tissue so the desired numbers of fasteners may be applied.

Once the gathered tissue 42 has been secured using the desired fastener, the device 10 may be removed from the patient. Removal of the gathered tissue 42 from the lumen 18 of catheter 12 may require the driveshaft 15 to be rotated in a second direction, counter to the first or gathering direction, to release the gathered tissue from the ribs 16. For this purpose, an actuating member on the handle may be operated to cause a "reverse" spinning of the driveshaft 15 to release the gathered tissue 42. With the tissue released from ribs 16, device 10 may readily be removed from the patient.

Figure 3:
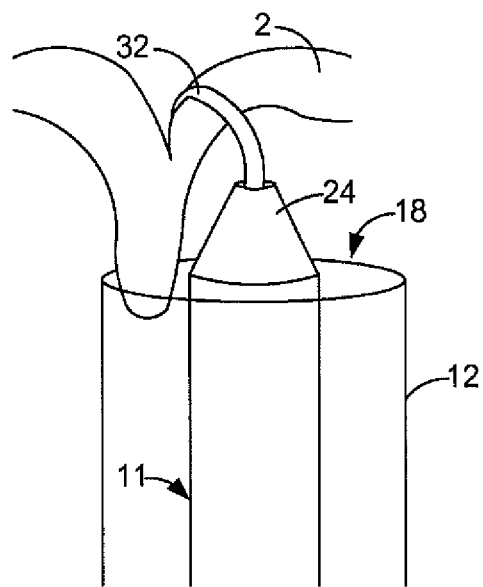
FIG. 3 is a highly schematic front view of the device of FIG. 2A with an optional wire.

In an alternative embodiment, shown in FIG. 3, device 10 may include an optional wire 32 to facilitate the collection of tissue. Specifically, wire 32 is configured to pull loose tissue close to the open distal end 19 of catheter 12. The wire 32 may be formed as a guidewire, and may include an arm or hook for pulling the loose tissue proximally. The core 11 may include a bore extending from its proximal end to its distal end, preferably along the central axis of the core, and the wire 32 may be disposed within the bore. It will be understood, however, that the wire 32 may be fashioned in other configurations and in different arrangements. For example, instead of being disposed along the central axis of core 11, the wire 32 may be positioned to one side of the core parallel with the core's central axis.

Wire 32 may be formed of a shape memory material such as, for example, nitinol. The use of a shape memory material allows the wire 32 to have a first, linear configuration when fully retracted within the core 11 or catheter 12, and a second, hook-shaped configuration when the wire is deployed. In the operation of this embodiment of device 10, the wire 32 is initially in a fully retracted position. If the vortex is incapable of drawing the loose tissue into the lumen 18 or if the loose tissue is too far from the open distal end 19 of catheter 12 to be influenced by the vortex, the wire 32 may be deployed from the catheter. As the wire 32 is deployed, its shape memory will bias its distal end into a hook shape, as seen in FIG. 3. The hook-shaped wire 32 may then be used to grab and pull the posterior leaflet 2 or anterior leaflet 3 close to the vortex or into the lumen 18, where it can be grabbed by the ribs 16 on rotating core 11.

As a result of the gathering of the loose or floppy tissue of leaflet 2, the shape of the leaflet may change. This tightening of the leaflet tissue may reduce the likelihood of prolapse and mitral valve regurgitation, thereby repairing the functionality of the valve.

In the devices shown in the figures, particular structures are shown that are adapted to grasp, secure, and repair heart valve leaflet tissue. The invention also contemplates the use of any alternative structures for such purposes, including structures having different lengths, shapes, and configurations.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for repair of a heart valve leaflet, the device comprising:
   an elongated body having a lumen extending therethrough in a longitudinal direction, a proximal end, and an open distal end, the elongated body having a plurality of apertures between the proximal and distal ends;
   a core having a proximal core end and a distal core end, the core including a tapered portion spaced from the distal core end, the core being disposed within the lumen and operable to spin about an axis extending in the longitudinal direction, the tapered portion being positioned adjacent at least one of the plurality of apertures and configured to direct fluid toward the at least one aperture when the core is spun; and
   a rib on an external surface of the core and positioned between the tapered portion and the distal core end, the rib comprising a resilient material,
   wherein the spinning of the core draws a portion of the heart valve leaflet into the open distal end of the elongated body and secures the portion of the heart valve leaflet to the core in a gathered configuration.

2. The device of claim 1, wherein the rib forms a helical pattern about the core.

3. The device of claim 1, wherein the resilient material is rubber.

4. The device of claim 1, further comprising a torque sensor connected to the core and operable to terminate spinning of the core upon sensing a predetermined maximum torque.

5. The device of claim 1, wherein the spinning of the core draws blood into the lumen through the open distal end of the elongated body, and the blood is expelled from the lumen through the plurality of apertures.

6. The device of claim 1, wherein the core includes a sidewall between the proximal core end and the distal core end, the sidewall having a circumference which decreases in size from the proximal core end to the distal core end.

7. The device of claim 1, further comprising a wire operable to pull a portion of the heart valve leaflet toward the open distal end of the elongated body.

8. The device of claim 7, wherein the core includes a bore extending from the proximal core end to the distal core end, the wire being slidably disposed in the bore for movement between a retracted position and an extended position.

9. The device of claim 8, wherein the wire is formed of a memory metal, a distal portion of the wire having a linear configuration when the wire is in the retracted position and a hook-shaped configuration when the wire is in the extended position.

10. The device of claim 1, further comprising:
    a motor operatively connected to the core for spinning the core at a desired speed.

11. The device of claim 1, further comprising at least one clip for securing the portion of the heart valve leaflet in the gathered configuration.

12. The device of claim 1, wherein at least the open distal end of the elongated body is formed from an echogenic material.

13. The device of claim 1, wherein the plurality of apertures are circumferentially spaced about the elongated body and adjacent to a proximal portion of the core.

* * * * *